(12) United States Patent
Aoba et al.

(10) Patent No.: US 9,827,127 B2
(45) Date of Patent: Nov. 28, 2017

(54) STENT DELIVERY SYSTEM

(71) Applicant: OLYMPUS CORPORATION, Tokyo (JP)

(72) Inventors: Daisuke Aoba, Saitama (JP); Hiroyoshi Watanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 463 days.

(21) Appl. No.: 14/543,158

(22) Filed: Nov. 17, 2014

(65) Prior Publication Data
US 2015/0073525 A1    Mar. 12, 2015

Related U.S. Application Data

(63) Continuation of application No. PCT/JP2014/062325, filed on May 8, 2014.

(30) Foreign Application Priority Data

May 10, 2013   (JP) .................. 2013-100743

(51) Int. Cl.
| | |
|---|---|
| A61F 2/06 | (2013.01) |
| A61F 2/966 | (2013.01) |
| A61F 2/95 | (2013.01) |
| A61F 2/82 | (2013.01) |
| A61F 2/848 | (2013.01) |
| A61F 2/94 | (2013.01) |
| A61F 2/04 | (2013.01) |

(52) U.S. Cl.
CPC ............ *A61F 2/966* (2013.01); *A61F 2/82* (2013.01); *A61F 2/95* (2013.01); *A61F 2/848* (2013.01);
(Continued)

(58) Field of Classification Search
CPC ............ A61F 2002/9511; A61F 2/95; A61F 2002/9505; A61F 2/966; A61F 2002/9517;
(Continued)

(56) References Cited

U.S. PATENT DOCUMENTS

2008/0287961 A1   11/2008   Miyamoto et al.
2008/0312829 A1   12/2008   Allen et al.
(Continued)

FOREIGN PATENT DOCUMENTS

EP       2 526 903 A1    11/2012
JP       2007-330796 A   12/2007
(Continued)

OTHER PUBLICATIONS

Extended Supplementary European Search Report dated Dec. 20, 2016 in related European Patent Application No. 14 79 5191.7.
(Continued)

*Primary Examiner* — Katherine M Shi
(74) *Attorney, Agent, or Firm* — Scully, Scott, Murphy & Presser, P.C.

(57) ABSTRACT

A stent delivery system for delivering a stent, the stent delivery system having a push catheter, a guide member, and an elongated stent securing material having a first portion arranged to a push catheter outer surface, a second portion, a third portion, and a fourth portion arranged to the push catheter outer surface, in that order. The first portion and the fourth portion are arranged to the push catheter outer surface such that only one of the first portion and the fourth portion is present on a cross-section plane orthogonal to the longitudinal axis. The stent delivery system is configured to have a secured configuration in which the guide member is arranged within a push catheter lumen and a stent lumen and through a loop formed by a section between the second portion and the third portion to secure the stent.

10 Claims, 5 Drawing Sheets

(52) U.S. Cl.
CPC ........... *A61F 2/94* (2013.01); *A61F 2002/041* (2013.01); *A61F 2002/8483* (2013.01); *A61F 2002/8486* (2013.01); *A61F 2002/9511* (2013.01); *A61F 2002/9665* (2013.01)

(58) Field of Classification Search
CPC ...... A61F 2002/9665; A61F 2002/011; A61M 25/01; A61M 2025/0004
USPC ................ 606/191, 194, 200; 623/1.11, 1.12
See application file for complete search history.

(56) References Cited

U.S. PATENT DOCUMENTS

2009/0312829 A1 12/2009 Aoba et al.
2012/0203325 A1 8/2012 Weisman et al.

FOREIGN PATENT DOCUMENTS

| | | |
|---|---|---|
| JP | 2009-297502 A | 12/2009 |
| JP | 2010-515486 A | 5/2010 |
| JP | 2011-251140 A | 12/2011 |
| JP | 5085199 B2 | 11/2012 |
| JP | 2013-31505 A | 2/2013 |
| JP | 2013-540502 A | 11/2013 |
| WO | 00/69498 A1 | 11/2000 |
| WO | 2006/019728 A2 | 2/2006 |
| WO | 2008/085714 A2 | 7/2008 |
| WO | 2012/039906 A1 | 3/2012 |

OTHER PUBLICATIONS

English Abstract of JP 2007-330796 A, dated Dec. 27, 2007.
Notice of Allowance dated Apr. 1, 2015 from Japanese Patent Application No. 2014-558342, together with an English language translation.

FIG. 7

STENT DELIVERY SYSTEM

CROSS REFERENCE TO RELATED APPLICATION

This application is a continuation claiming priority on the basis of Japanese Patent Application No. 2013-100743 filed in Japan on May 10, 2013 and based on PCT/JP2014/062325 filed on May 8, 2014. The contents of both the Japanese Patent Application and the PCT Application are incorporated herein by reference.

BACKGROUND

The present invention relates to a stent delivery system.

In the related art, a stent delivery system for arranging a tubular stent at a desired position within a living body is known (for an example, refer to the Japanese Patent No. 5085199).

In the stent delivery system described in Japanese Patent No. 5085199, a push catheter is extracted from an endoscope after the stent is pushed into inside the body by the push catheter to be indwelled therein.

SUMMARY

A first aspect of the present invention provides a stent delivery system for delivering a stent, wherein the stent has a stent outer surface and a stent inner surface, wherein the stent defines a stent through hole connecting the stent outer surface and the stent inner surface, and wherein the stent has a proximal end face, and the proximal end face of the stent defines a proximal opening of the stent lumen, wherein the stent delivery system comprises: a push catheter having a push catheter outer surface and a push catheter inner surface, wherein the push catheter has a distal end and a proximal end that together define a longitudinal axis, wherein the push catheter inner surface defines a push catheter lumen, wherein the push catheter has a distal end face, and the distal end face of the push catheter defines a distal opening of the push catheter lumen, wherein the push catheter defines a first through hole connecting the push catheter outer surface and the push catheter inner surface, and the first through hole is arranged at a first position along the longitudinal axis, and wherein the push catheter defines a second through hole connecting the push catheter outer surface and the push catheter inner surface, and the second through hole is arranged at a second position along the longitudinal axis different from the first position; a guide member configured to be retractably inserted within the stent lumen and the push catheter lumen; and an elongated stent securing material having: a first portion arranged to the push catheter outer surface, a second portion, a third portion, and a fourth portion arranged to the push catheter outer surface, in that order, a first section between the first portion and the second portion, a second section that forms a loop between the second portion and the third portion, and a third section between the third portion and the fourth portion, wherein the first portion and the fourth portion are arranged to the push catheter outer surface such that only one of the first portion and the fourth portion is present on a cross-sectional plane orthogonal to the longitudinal axis, wherein the stent delivery system is configured to have a secured configuration in which: the stent and push catheter are arranged in series such that the proximal end face of the stent faces the distal end face of the push catheter, the loop formed by the second section is passed through the stent through hole from the stent outer surface into the stent lumen, and the guide member is arranged within the push catheter lumen and the stent lumen and through the loop to secure the stent.

DETAILED DESCRIPTION OF THE EMBODIMENTS

Figure 1:
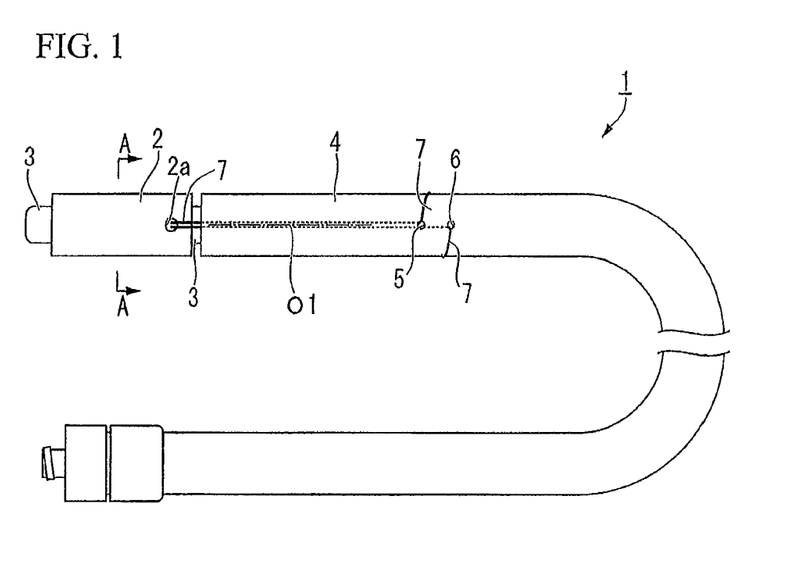
FIG. 1 is a plan view of a stent delivery system of an embodiment of the present invention.
Figure 2:
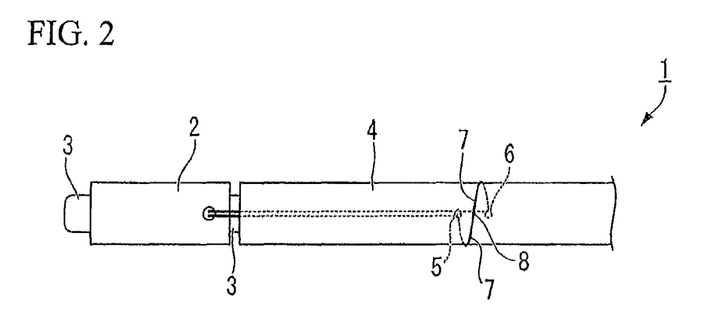
FIG. 2 is a bottom view of the stent delivery system.
Figure 3:
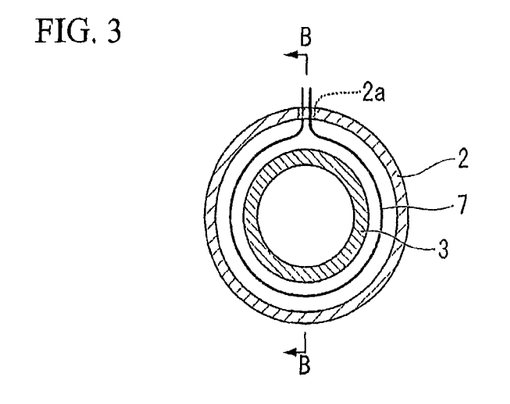
FIG. 3 is a cross-sectional view in line A-A of FIG. 1.
Figure 4:
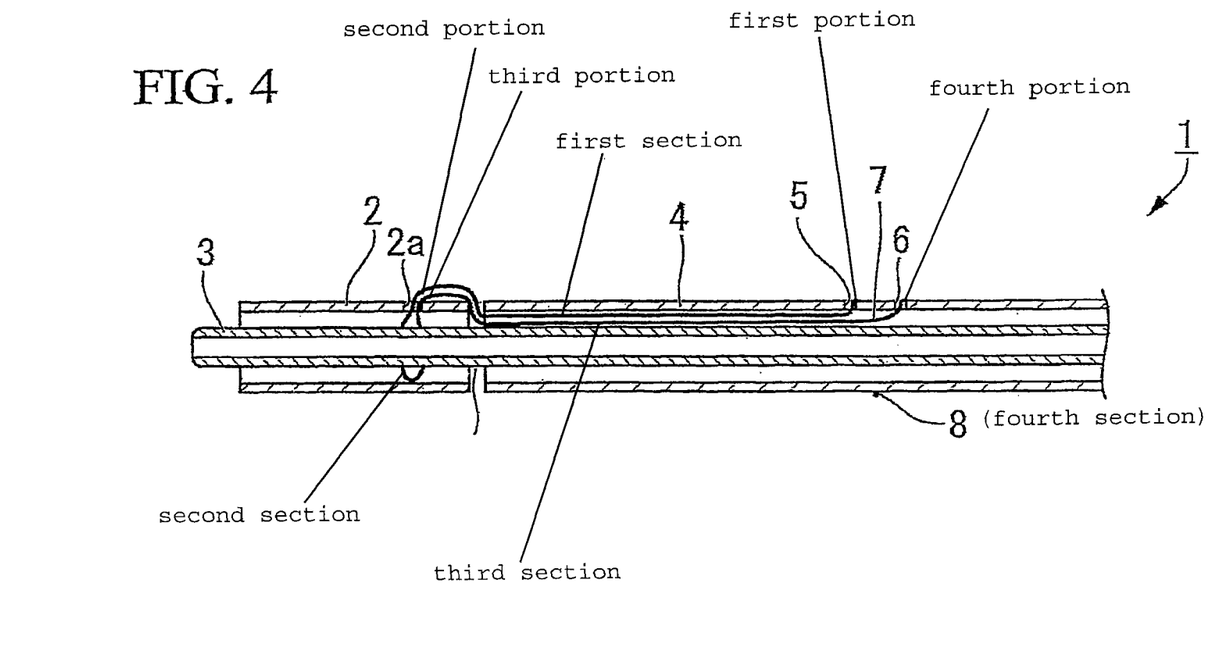
FIG. 4 is a cross-sectional view in line B-B of FIG. 3.
Figure 5:
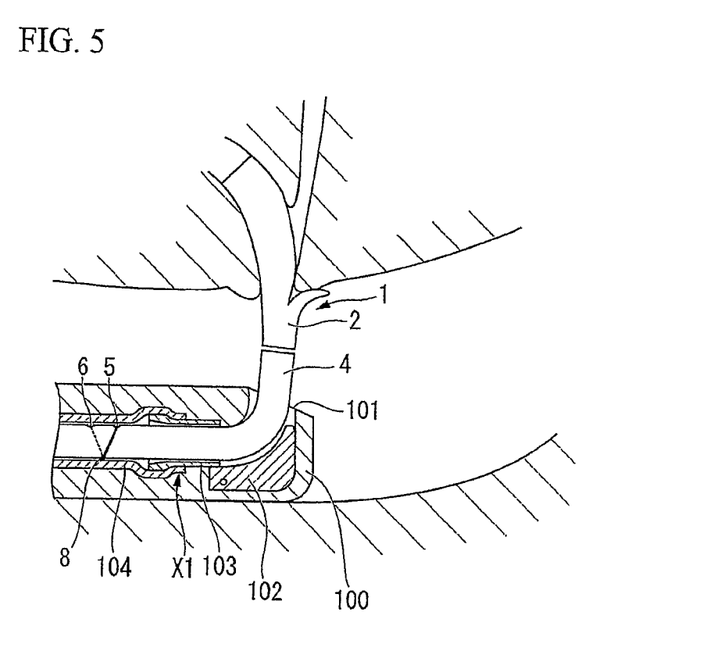
FIG. 5 is an explanatory view for illustrating the positional relationship between a first passage and a second passage in the stent delivery system.
Figure 6:
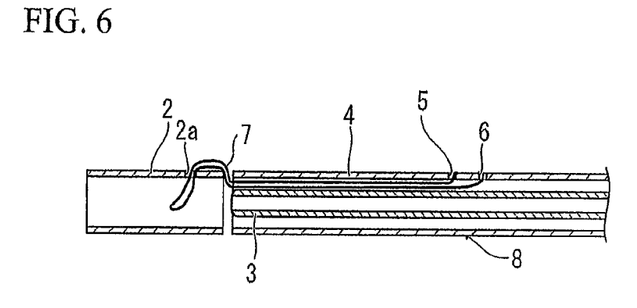
FIG. 6 is a cross-sectional view showing a state after the release of a stent in the stent delivery system.
Figure 7:
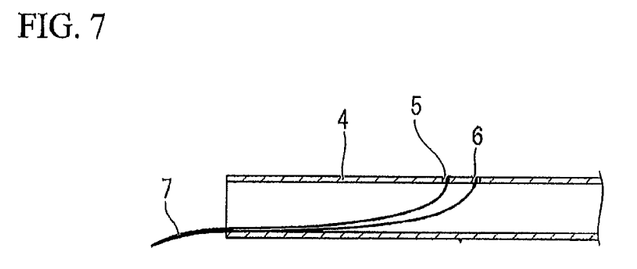
FIG. 7 is a cross-sectional view showing a state after the release of the stent in the stent delivery system.

An embodiment of a stent delivery system 1 of the present invention will be described. FIG. 1 is a plan view of the stent delivery system 1 of the present embodiment. FIG. 2 is a bottom view of the stent delivery system 1. FIG. 3 is a cross-sectional view in line A-A of FIG. 1. FIG. 4 is a cross-sectional view in line B-B of FIG. 3. FIG. 5 is an explanatory view for illustrating the positional relationship between a first passage and a second passage in the stent delivery system. FIG. 6 is a cross-sectional view showing a state after the release of a stent 2 in the stent delivery system 1. FIG. 7 is a cross-sectional view showing a state after the release of the stent 2 in the stent delivery system 1 and after the stent 2 comes off a connecting member 7.

In the stent delivery system 1 of the present embodiment shown in FIG. 1, a tubular stent 2 is arranged at a desired position within a living body.

The stent 2, which can be applied to the stent delivery system 1 of the present embodiment, is formed with a through-hole 2a that allows the inside and outside of the stent 2 to communicate with each other and couples the stent delivery system 1 and the stent 2. In the present embodiment, the through-hole 2a is provided in the vicinity of an end portion of the stent 2. When the stent 2 is inserted into the stent delivery system 1, the stent 2 is connected to the stent delivery system 1 with the stent 2 being directed to the stent delivery system 1 so that the side of the stent where the through-hole 2a is formed gets closer to a distal end of the stent delivery system 1. Additionally, the shape of the stent 2 may have flaps formed at both ends or may be a simple tubular shape with no flap. The material of the stent 2 is not particularly limited. For example, the stent 2 may be made of resin having flexibility.

As shown in FIG. 1, the stent delivery system 1 includes a guide catheter 3, a push catheter 4, and a connecting member 7.

The guide catheter 3 is an elongated member that is inserted into the stent 2 and inserted into the living body together with the stent 2. The guide catheter 3 may be solid or tubular. The guide catheter 3 has flexibility.

The push catheter 4 is a tubular member provided in order to push the stent 2 along the guide catheter 3. The push catheter 4 has an internal diameter such that the guide catheter 3 can be freely advanced and retracted within the push catheter. Moreover, a gap that the guide catheter 3 can be advanced and retracted with respect to the push catheter 4 is provided between the guide catheter 3 and the push catheter 4 even in a state where both the guide catheter 3 and the connecting member 7 are disposed within the push catheter 4. The push catheter 4 is inserted into the living body together with the guide catheter 3 after the guide catheter 3 is inserted into the push catheter.

Additionally, the push catheter 4 has a first passage 5 formed with a through-hole (first through-hole) that allows the inside and the outside of the push catheter 4 to communicate with each other, and a second passage 6 formed with a through-hole (second through-hole) that allows the inside and the outside of the push catheter 4 to communicate with each other at a position different from the first passage 5. The first passage 5 and the second passage 6 are passages into which the connecting member 7 is inserted.

Additionally, the first passage 5 and the second passage 6 are arranged on a line that is parallel to a central axis O1 of the push catheter 4 and open, in the external surface of the push catheter 4. There is a space in between the first passage 5 and the second passage 6. Accordingly, compared to a case where the first passage 5 and the second passage 6 are located in parallel along the circumferential direction of the push catheter 4, the distance of the first passage 5 and the second passage 6 is easily increased, and it is possible to prevent a situation where, when the connecting member 7 is caught in an endoscope or other devices and an external force acts on the push catheter 4, the push catheter 4 is completely torn and the connecting member 7 comes off the push catheter 4.

Additionally, in the present embodiment, a proximal end of the push catheter 4 and a proximal end of the guide catheter 3 are enabled to be coupled to each other. The push catheter 4 and the guide catheter 3 can be integrally advanced and retracted in a state where the proximal end of the push catheter 4 and the proximal end of the guide catheter 3 are coupled to each other.

The connecting member 7 is a member for connecting the stent 2 to the push catheter 4. The connecting member 7 is a flexible thread having a closed loop shape. In the present embodiment, the thread used as the connecting member 7 has a closed loop shape as both ends thereof are tied together by one knot 8 shown in FIG. 2. The materials of the thread used as the connecting member 7 are not particularly limited if materials that do not affect the living body are provided. For example, the connecting member 7 may be a thin wire made of resin or metal.

Additionally, the distances of the first passage 5 and the second passage 6 from a distal end of the push catheter 4 are set to optimal distances in correspondence with the structure of an endoscope to which the stent delivery system 1 is applied.

For example, as shown in FIG. 5, when the stent delivery system 1 is applied to a side view type endoscope 100, it is preferable that the first passage 5 and the second passage 6 be located closer to proximal end side than forceps raising base 102 in the side view type endoscope 100, in a state where the distal end of the push catheter 4 is delivered from a distal end of a treatment tool channel 101 of the side view type endoscope. Additionally, in a case where there is a step in the inner surface of the treatment tool channel 101 on the distal end side due to a connecting portion X1 or the like between a rigid portion 103 of a distal end of the endoscope and a channel tube 104, when the distal end of the push catheter 4 is delivered to a position suitable for the indwelling of the stent 2, it is preferable that the first passage 5 and the second passage 6 be located closer to the proximal end side than this step (a portion shown by symbol X1 in FIG. 5).

More specifically, when the length from an opening portion of the distal end of the treatment tool channel 101 to a proximal end of the forceps raising base 102 is about 10 mm, and the length from the opening portion of the distal end of the treatment tool channel 101 to a proximal end of the stepped portion (portion shown by symbol X1 in FIG. 5) of the treatment tool channel 101 is about 20 mm, the first passage 5 and the second passage 6 are provided at a position apart from the distal end of the push catheter 4 by about 55 mm. In this case, even if the distal end of the push catheter 4 is made to protrude by about 20 mm from the opening portion of the treatment tool channel when the stent 2 is arranged, the first passage 5 and the second passage 6 are located closer to the proximal end side than the forceps raising base 102 and the stepped portion (portion shown by symbol X1 in FIG. 5) of the treatment tool channel 101.

By setting the positions of the first passage 5 and the second passage 6 as described above, the effect of preventing a phenomenon in which the connecting member 7 extending from the inside of the push catheter 4 through the first passage 5 and the second passage 6 to the outside is cut or the knot 8 is untied is exhibited.

Next, a state where the connecting member 7 is attached to the push catheter 4 will be described in detail with reference to FIGS. 3 and 4.

Only one thread is inserted through the first passage 5, and only one thread is inserted through the second passage 6. Accordingly, the thread used as the connecting member 7 is configured so as not to come off the push catheter 4 unless either the thread is cut or the push catheter 4 is torn. The connecting member 7 (thread) pulled out of the push catheter 4 from the first passage 5 and the second passage 6 is fixed to an external surface of the push catheter 4. The thread pulled out from the inside of the push catheter 4 through the first passage 5 to the outside and the thread pulled out from the inside of the push catheter 4 through the second passage 6 to the outside extend in opposite directions along the circumferential direction of the push catheter 4, in the circumferential direction of the push catheter 4. In the present embodiment, the knot 8 of the connecting member 7 (thread) is disposed on the outside of the push catheter 4, and the knot 8 is fixed by adhesion. Additionally, the knot 8 may be adhered and fixed to the outer peripheral surface of the push catheter 4.

Additionally, both the connecting member 7 pulled in from the outside of the push catheter 4 via the first passage 5 to the inside of the push catheter and the connecting member 7 pulled in from the outside of the push catheter 4 via the second passage 6 to the inside of the push catheter are able to extend from the distal end of the push catheter 4 through the inside of the push catheter 4. The connecting member 7 extended from the distal end of the push catheter 4 has a U shape that is folded back in the vicinity of the distal end of the push catheter 4. The extending length of the connecting member 7 from the distal end of the push catheter 4 is set according to the shape of the stent 2.

Next, a state where the connecting member 7 is attached to the stent 2 and the guide catheter 3 will be described in detail.

As shown in FIG. 4, in the use of the stent delivery system 1, before the release of the stent 2, the stent 2 is disposed parallel to the push catheter 4 so as to be capable of coming into contact with the distal end of the push catheter 4, and the guide catheter 3 is inserted through the inside of the stent 2 and the inside of the push catheter 4. Moreover, before the release of the stent 2, the connecting member 7 (thread) is fixed to the push catheter 4, both the thread extending from the first passage 5 and the thread extending from the second passage 6 are delivered together with the guide catheter 3 from the distal end of the push catheter 4, and extends to the inside of the stent 2 through the through-hole 2a of the stent 2 along an external surface of the stent 2. The connecting member 7 extending to the inside of the stent 2 has a loop shape surrounding the guide catheter 3 inside the stent 2.

In this state, the stent 2 is locked to the connecting member 7 built between the push catheter 4 and the guide catheter 3, and the stent 2 is held by the thread so that the stent 2 does not fall off the stent delivery system 1.

As shown in FIGS. 4 and 6, in the use of the stent delivery system 1, when the stent 2 is released at a desired position within the living body, the guide catheter 3 is moved to the proximal end side after the stent 2 is arranged at the desired position. Accordingly, the guide catheter 3 slips out from the connecting member 7 (thread) having the loop shape surrounding the guide catheter 3 inside the stent 2.

Subsequently, the push catheter 4 and the guide catheter 3 are moved to the proximal end side. Then, the connecting member 7 (thread) fixed to the push catheter 4 is pulled out of the stent 2 through the through-hole 2a of the stent 2. Then, the thread comes off the stent 2.

The thread that has come off the stent 2, as shown in FIG. 7, is pulled back to the proximal end side together with the push catheter 4 in a state where the thread is supported by an opening end portion in the distal end of the push catheter 4. At this time, a distal end portion of the thread used as the connecting member 7 is in a state where the distal end portion extends in a distal end direction from the opening end portion of the distal end of the push catheter 4.

In the related art, in a stent delivery system that holds a stent using thread, the thread may be entangled in an endoscope or other devices if the thread, which is brought into a state where the thread is delivered from a distal end of a push catheter after the release of the stent, is long. For example, in the case of the thread having folding within the stent as in Patent Document 1, the thread is long compared to the thread that is the connecting member of the present embodiment. Thus, the thread becomes easily entangled. Additionally, when the push catheter is provided with only one passage for allowing the thread to pass through the push catheter, and a closed loop-shaped thread is hung between the passage and a distal end opening of the push catheter, the thread may be deflected so as to spread in a radial direction of the push catheter after the release of the stent. Even in this case, the thread becomes easily entangled.

In the present embodiment, the thread is shortened by forming the loop surrounding the guide catheter 3 within the stent 2, and is brought into a state where the thread is supported by the opening end portion in the distal end of the push catheter 4 after the release of the stent 2. Thus, as compared to the above related-art configuration, a probability that the thread may be entangled in the endoscope and other devices in the process of extracting the push catheter 4 from the endoscope after the release of the stent 2 can be lowered.

Although the embodiment of the present invention has been described above with reference to the drawings, specific configuration is not limited to the embodiment. Additions, omissions, substitutions, and other modifications of components can be made as long as there is no departure from the concept of the present invention. Accordingly, the present invention is not considered to be limiting from the foregoing description, and is only limited by the scope of the appended claims.

For example, in the above-described embodiment, the stent 2 is provided with the through-hole 2a for allowing the connecting member 7 to pass therethrough. However, if there is the through-hole that allows the inside and the outside of the stent 2 to communicate with each other irrespective of a purpose, the stent 2 can be suitably indwelled through the connecting member 7 similar to the above embodiment.

Additionally, the through-hole formed in the stent 2 may be machined so that resistance decreases when the thread is pulled out from the through-hole.

Additionally, in the above-described embodiment, the passages on the push catheter 4 formed in order to allow the connecting member 7 to pass through are two including the first passage 5 and the second passage 6. However, only one passage may be provided. In that case, two connecting members can be connected outside the push catheter 4 by pulling out the connecting members through one passage similar to the above-described example.

Additionally, the thread used as the connecting member 7 may have elasticity. If the thread used as the connecting member 7 has elasticity, the thread delivered from the distal end of the push catheter 4 does not hang down easily, and is held in the loop shape that is directed to the distal end direction of the push catheter 4. Thus, the thread is not further easily entangled.

Although the preferred embodiments of the present invention have been described above, the present invention is not limited to these embodiments. Additions, omissions, substitutions, and other modifications of components can be made without departing to the invention as long as there is no departure from the concept of the invention. The invention is not to be considered as being limited by the foregoing description, and is limited only by the scope of the appended claims.

What is claimed is:

1. A stent delivery system for delivering a stent,
   wherein the stent has a stent outer surface and a stent inner surface,
   wherein the stent inner surface defines a stent lumen,
   wherein the stent defines a stent through hole connecting the stent outer surface and the stent inner surface, and
   wherein the stent has a proximal end face, and the proximal end face of the stent defines a proximal opening of the stent lumen,
   wherein the stent delivery system comprises:
   a push catheter having a push catheter outer surface and a push catheter inner surface,
   wherein the push catheter has a distal end and a proximal end that together define a longitudinal axis,
   wherein the push catheter inner surface defines a push catheter lumen,
   wherein the push catheter has a distal end face, and the distal end face of the push catheter defines a distal opening of the push catheter lumen,
   wherein the push catheter defines a first through hole connecting the push catheter outer surface and the push catheter inner surface, and the first through hole is arranged at a first position along the longitudinal axis, and
   wherein the push catheter defines a second through hole connecting the push catheter outer surface and the push catheter inner surface, and the second through hole is arranged at a second position along the longitudinal axis different from the first position;
a guide member configured to be retractably inserted within the stent lumen and the push catheter lumen; and
an elongated stent securing material having:
  a first portion arranged to the push catheter outer surface, a second portion, a third portion, and a fourth portion arranged to the push catheter outer surface, in that order,
  a first section between the first portion and the second portion, a second section that forms a loop between the second portion and the third portion, and a third section between the third portion and the fourth portion,
wherein the stent delivery system is configured to have a secured configuration in which:
  the stent and push catheter are arranged in series such that the proximal end face of the stent faces the distal end face of the push catheter,
  the loop formed by the second section is passed through the stent through hole from the stent outer surface into the stent lumen, and
  the guide member is arranged within the push catheter lumen and the stent lumen and through the loop,
  wherein the first section extends from the first portion through the first through hole of the push catheter into the push catheter lumen and further extends out through the distal opening of the push catheter lumen, and
  wherein the third section extends from the fourth portion through the second through hole of the push catheter into the push catheter lumen and further extends out through the distal opening of the push catheter lumen.

2. The stent delivery system according to claim 1, wherein in the secured configuration:
  the first section extends from the distal opening of the push catheter lumen to be arranged on the stent outer surface, and the third section extends from the distal opening of the push catheter lumen to be arranged on the stent outer surface, and
  the guide member is arranged within the push catheter lumen and the stent lumen and through the loop to secure the stent by limiting relative movement of the proximal end face of the stent and the distal end face of the push catheter, and
wherein the stent delivery system is configured to have a released configuration in which the guide member is retracted through the loop to release the stent by permitting retraction of the second section of the elongated stent securing material through the stent through hole and permitting relative movement of the proximal end face of the stent and the distal end face of the push catheter.

3. The stent delivery system according to claim 2, wherein the first portion and the fourth portion are arranged to the push catheter outer surface such that only one of the first portion and the fourth portion is present on a cross-sectional plane orthogonal to the longitudinal axis.

4. The stent delivery system according to claim 1, wherein the first portion of the elongated stent securing material extends away from the first through hole in a first circumferential direction around the circumference of the push catheter outer surface, and
wherein the fourth portion of the elongated stent securing material extends away from the second through hole in a second circumferential direction around the circumference of the push catheter outer surface.

5. The stent delivery system according to claim 4, wherein the elongated stent securing material has a fourth section connecting the first portion and the fourth portion of the elongated stent securing material.

6. The stent delivery system according to claim 5, wherein the fourth section of the elongated stent securing material is a knot connected to the push catheter outer surface.

7. The stent delivery system according to claim 1, wherein the first through hole and the second through hole are formed on a through hole axis that is parallel to the longitudinal axis.

8. The stent delivery system according to claim 1, wherein in the secured configuration, the push catheter, guide member and elongated stent securing material are configured to deliver the stent through a distal opening of a channel formed in an insertion portion of an endoscope.

9. The stent delivery system according to claim 8, wherein the insertion portion has a distal end and a proximal end that together define an insertion portion axis,
wherein the channel of the insertion portion has a channel central axis that extends through the distal opening of the channel in a direction that deviates from the insertion portion axis,
wherein a raising base that forms a portion of the channel is arranged in the insertion portion at a position along the channel central axis that is a first predetermined distance proximal to the distal opening of the channel, and
wherein each of:
  a first through hole distance between the first through hole and the distal end face of the push catheter along the longitudinal axis, and
  a second through hole distance between the second through hole and the distal end face of the push catheter along the longitudinal axis, is longer than the first predetermined distance.

10. The stent delivery system according to claim 1, wherein the elongated stent securing material has a fourth section connecting the first portion and the fourth portion of the elongated stent securing material.

* * * * *